United States Patent [19]

Petite et al.

[11] Patent Number: 4,958,008

[45] Date of Patent: Sep. 18, 1990

[54] PROCESS FOR CROSSLINKING OF COLLAGEN BY INTRODUCTION OF AZIDE GROUPS AS WELL AS TISSUES AND BIOMATERIALS OBTAINED BY USE OF THE PROCESS

[76] Inventors: Hervé Petite, 118 Avenue Saint-Exupéry, 69500 Bron; Philippe Menasche, 1 rue du Regard, 75006 Paris; Alain Huc, 26 Chemin des Fonds, 69110 Sainte Foy Les Lyon, all of France

[21] Appl. No.: 216,407

[22] Filed: Jul. 7, 1988

[30] Foreign Application Priority Data

Jul. 8, 1987 [FR] France ................... 87 10317

[51] Int. Cl.$^5$ ............................................. C07K 15/20
[52] U.S. Cl. ..................................... 530/356; 106/155; 106/161; 128/DIG. 8; 604/368
[58] Field of Search ................. 530/356; 106/155, 161; 128/DIG. 8; 604/368

[56] References Cited

U.S. PATENT DOCUMENTS

| 3,293,237 | 12/1966 | Wiegand | 530/356 |
| 3,443,261 | 5/1969 | Battist | 530/356 |
| 4,280,954 | 7/1981 | Yannas | 530/356 |

FOREIGN PATENT DOCUMENTS

| 2153667 | 5/1973 | France | 530/356 |
| 2559666 | 8/1985 | France | |

*Primary Examiner*—Howard E. Schain
*Attorney, Agent, or Firm*—Browdy & Neimark

[57] ABSTRACT

This process, which essentially comprises the following steps:
 esterification of the free acid groups of the collagen,
 transformation of the esterified groups into hydrazides groups,
 transformation of the hydrazide groups into azide groups by the action of nitrous acid, is characterized in that each step is separated by a rinsing in an aqueous salt solution, and in that the step of transformation of esterified groups into azide groups and the step of transformation of hydrazide groups into azide groups by the action of nitrous acid, are performed in the presence of salt.

15 Claims, 3 Drawing Sheets

PROCESS FOR CROSSLINKING OF COLLAGEN BY INTRODUCTION OF AZIDE GROUPS AS WELL AS TISSUES AND BIOMATERIALS OBTAINED BY USE OF THE PROCESS

BACKGROUND OF THE INVENTION

1. Field of the invention

This invention relates to a process for crosslinking of collagen by introduction of azide groups as well as tissues and biomaterials obtained by using the process.

2. The Prior Art

Replacement of a pathological cardiac valve in man now essentially resorts to two types of substitutes: mechanical prostheses and heterologous biological valves (also called heterografts or bioprotheses). If the former have the advantage of an almost unlimited life, they have as the main limitation a permanent thromboembolic risk requiring an anticoagulant treatment for life whose own (hemorrhagic) risks contribute in no small part to the morbidity and overall mortality observed in patients wearing these protheses.

On the contrary, bioprotheses today have clearly shown their slight thrombogenicity in the absence of anticoagulant treatment. On the other hand, their life is greatly burdened by the occurrence of tissue calcification which, alone or in association with fatigue lesions, lead to a reintervention in an average period of 6 years, this period moreover being shorter in younger patients.

Also, one of the main trends in research in the matter of artificial valves today is focused on the development of techniques making it possible to retard the deterioration of the bioprotheses.

Obviously, this deterioration is a multifactor phenomenon, some factors, "linked to the host," being difficult to control.

However, it clearly appears that the mode of treatment of the tissue at the time of production of the valve, a treatment on which it is possible to intervene, can play a primordial role.

At present, regardless of the animal origin of this tissue (aortic valves of hogs or bovine pericardium), its treatment almost always resorts, for the models of bioprotheses now on the market, to tanning techniques using glutaraldehyde (GTA).

Actually, the aptitude is known of this tanning agent for creating solid intermolecular bonds which enable the tissue thus treated to exhibit the required mechanical properties and to resist "in vivo" enzymatic degradation.

An additional argument for using glutaraldehyde is that, by the creation of bonds between the collagen molecules, it masks some antigenic determinants which makes it possible to limit the antigenicity of the tissue.

Although the exact relationship between glutaraldehyde and calcification has not yet been totally explained, there is certainly a causality relationship. Actually it appears, that contrary to untreated implants, implants of hog aortic valves treated with GTA severely calcify.

Further, it has been shown that hog aortic valves, or calf pericardium, both treated with GTA, calcify in the same way in rats (Schoen et al., Am. J. Path. 1986, 193, pp. 134–145).

Although factors regulating this calcification mechanism and depending on the host and the implant have been brought out (by Levy, Schoen, Howard et al), it has not yet been possible to determine the underlying mechanism of this calcification.

Moreover, the role of the collagen side groups was studied by Urist in 1966 and Glimcher in 1968.

Thus Urist was able to show that treatment of the tendon of a rat tail in solutions of inorganic salts such as $CaCl_2$, $SrCl_2$ or organic cations, which block carboxylic groups of side chains, effectively inhibit calcification of the tendons implanted in the hypercalcemic rat.

Glimcher tried to inhibit calcification of collagen of the bone in vitro by esterifying carboxylic groups. In this case, blocking of the groups inhibits calcification. However, a part of this inhibition would probably be due to dehydration of the tissue in methanol.

SUMMARY OF THE INVENTION

The object of the invention is to propose a chemical process able to assure blocking of the acid collagen side groups and to avoid the use of glutaraldehyde whose drawback is a certain toxicity, besides inducing calcification.

In FR-A-2 559 666 the inventors had already proposed a process for production of collagen tubes according to which, when dried, the collagen tube was subjected to a crosslinking by thorough dehydration in an oven at about 80° C. under a vacuum of about 0.1 mm of mercury for about 24 hours.

The crosslinked collagen tube was then subjected to a treatment making it possible to introduce azide groups into the molecule yet without causing the coupling of the collagen with any molecule.

The inventors continued their research in this direction particularly by trying to eliminate the preliminary step of crosslinking by dehydration while arriving at a blocking of the acid end groups of collagen, improving the mechanical properties of the resulting tissue and avoiding any resolubilizing of the collagen, the aim being to obtain a degree of crosslinking of the collagen equivalent to that obtained with glutaraldehyde, thus allowing a reduction to be expected of the phenomena of calcification and, of course, the phenomena of toxicity connected with the secondary release of the glutaraldehyde.

The interest of the process is reinforced by the fact that it does not replace glutaraldehyde with another tanning agent which could pose specific problems, since it creates crosslink bonds between the collagen side chains without permanently introducing a foreign chemical agent.

Thus, on the conceptual plane, the process according to the invention seems to offer a new way to the extent that it replaces the traditional fixing of the tissue, invariably based on the use of glutaraldehyde, with a fixing based on a modification of the structure of the collagen side groups obtained without resorting to any tanning agent.

The inventors were able to determine during their research that it was possible to block effectively the collagen side groups to avoid any resolubilizing of the latter and to improve considerably the mechanical properties of the biomaterials obtained, if a chemical crosslinking of the collagen is performed by introducing azide groups in the presence of sodium chloride.

According to the invention, the process of crosslinking the collagen by introducing azide groups which essentially comprises the following steps:

esterification of the free acid groups of the collagen, transformation of the esterified groups into hydrazide groups, transformation of the hydrazide groups into azide groups by the action of nitrous acid, is characterized in that each step is separated by a rinsing thanks to an aqueous salt solution.

According to a preferred embodiment of the invention, the steps of transformation of esterified groups into hydrazide groups and hydrazide groups into azide groups by the action of nitrous acid, are performed in the presence of salt.

The salt is selected from the alkaline metals salts not denaturing the collagen. The aqueous salt solutions are used in concentrations between 3 and 15%. The crosslinking reaction by introducing azide groups is performed on uncrosslinked collagens.

The invention also relates to the biomaterials obtained by using the above process and particularly bioprotheses as well as any other biomaterial with a base of crosslinked collagen thus obtained, such as films, sponges, tubes, etc.

DESCRIPTION OF THE PREFERRED EMBODIMENT

Figure 1:
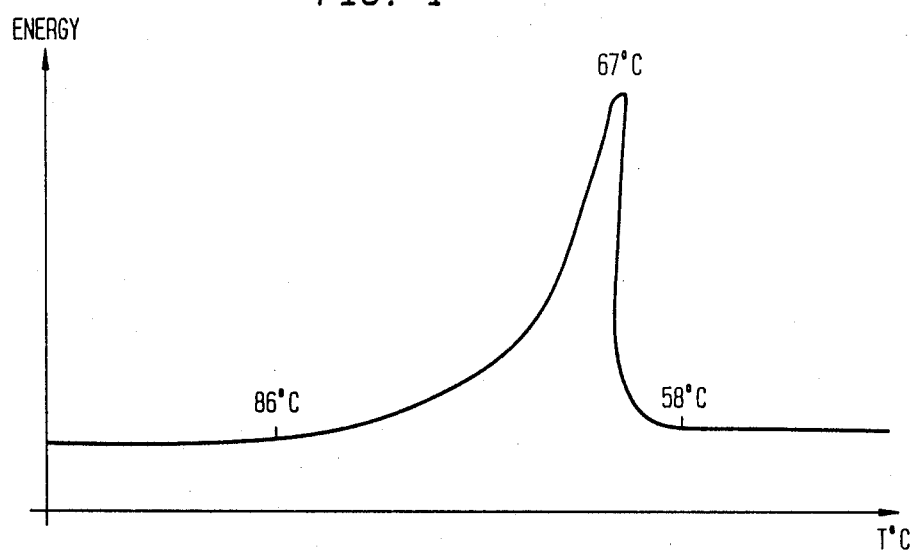
FIGS. 1 and 2 are differential calorimetric curves programmed respectively for a fresh untreated pericardium and for a pericardium treated according to the invention.

This invention will be better understood and its advantages will come out from the following description of an embodiment according to the invention.

A. Preparation of the starting material

Pericardia are taken, at slaughter houses, from 100-day-old calves less than an hour after they are killed. These pericardia are then degreased, sorted, washed in a 0.9% aqueous solution of sodium chloride.

B. Crosslinking of collagen by introducing azide groups

This crosslinking reaction can be summarized as follows:

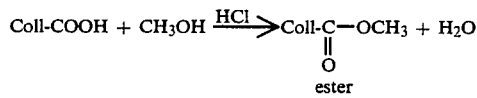

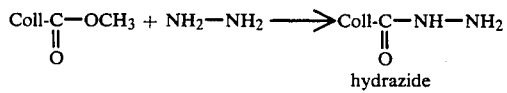

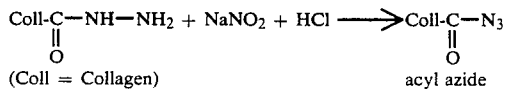

(Coll = Collagen)

The first step, esterification of the carboxylic groups is performed by immersion of the samples in a methanol solution containing 0.2 mole of hydrochloric acid at ambient temperature for 7 days.

Two rinsings are performed in methanol without acid.

Then two rinsings are performed with a 6% aqueous solution of sodium chloride (step 2).

The samples are then immersed in a 1% hydrazine solution with 6% NaCl overnight to obtain hydrazides from the esterified groups. The reaction takes place at ambient temperature (step 3).

Then a rinsing is performed at 4° C. with a 6% aqueous solution of sodium chloride (step 4).

The next step (step 5) consists in immersing the resulting samples in a solution containing 0.3 mole of hydrochloric acid and 0.5 mole of sodium nitrite in a 6% aqueous solution of sodium chloride.

The samples are then rinsed (step 6) to eliminate the acid completely; they are then kept for four hours at ambient temperature in a 6% borate-sodium chloride (step 7).

The acylazides form the carboxylic groups of collagen side chains will thus be able to react with amino groups, essentially lysine, to form an amide bond. Thus crosslinking bonds are created inside the collagen network.

The samples are finally incubated, at ambient temperature, in a 9% borate-glycine-sodium chloride buffer for at least three hours.

To obtain a sterile biomaterial, it is preferable to keep the resulting samples in 70 alcohol.

The influence exerted by the addition of sodium chloride during the various steps of the process will now be studied.

(1) Differential Scanning Calorimetry Study

Differential scanning calorimetric (DSC) analysis makes possible a dynamic calorimetric study of the test samples.

The technique consists in measuring, during a linear rise in temperature, the difference in energy that must be supplied to a sample and a reference to keep them at an identical temperature. When the protein is denatured, a heat absorption peak appears on the recorder. Actually, the static twist coil transition is endothermic for collagen.

There are thus defined:
the denaturing starting temperature
the denaturing peak temperature
the denaturing end temperature.
The study was made comparatively:
on a film and a control pericardium, untreated (control)
on a film and a pericardium subjected to different crosslinking steps by introducing azide groups in the presence of water,
on a film and on a pericardium subjected to different crosslinking steps by introducing azide groups according to the invention, i.e., in the presence of a 6% aqueous solution of sodium chloride (NaCl),
on a film and on a treated pericardium with a 0.6% solution of glutaraldehyde (GTA).

The results are gathered in table I below:

TABLE I

| Film | Tem. in °C. Starting | Tem. in °C. Peak | Tem. in °C. End |
|---|---|---|---|
| control | 39.15 | 49.1 | 66.1 |
| water | 53.6 | 63.8 | 76.6 |

TABLE I-continued

| Film | Tem. in °C. Starting | Tem. in °C. Peak | Tem. in °C. End |
|---|---|---|---|
| 6% NaCl | 65.5 | 74.3 | 83 |
| 6% GTA | 71.1 | 79.1 | 86.4 |
| Pericardium | | | |
| control | 53.6 | 62.8 | 73.6 |
| water | 70 | 75.7 | 84.1 |
| 6% NaCl | 78 | 81.4 | 89.1 |
| 6% GTA | 82 | 85.3 | 93.8 |

Figure 2:
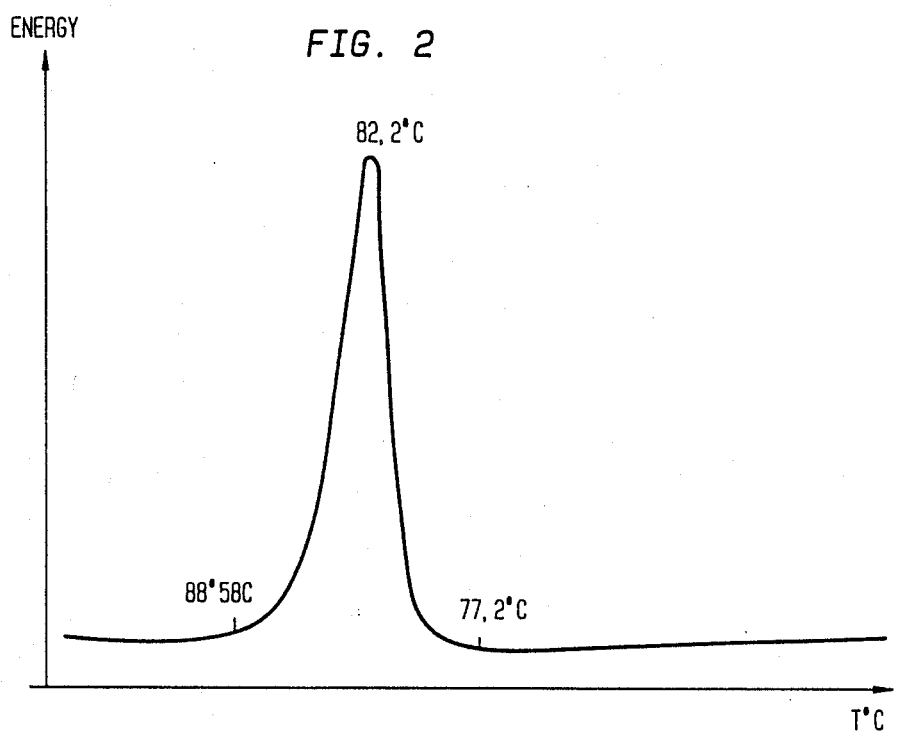

FIG. 1 represents the energy/temperature curve for a fresh pericardium and FIG. 2 the same curve for pericardium treated by the process according to the invention, in a medium not containing sodium chloride in steps 2, 3, 4, 5, 6, this pericardium has a denaturing starting temperature of 70° C. at the end of the treatment.

A pericardium treated under the same conditions but in the presence of 6% NaCl in steps 2, 3, 4, 5, 6 according to the invention, has a denaturing starting temperature of 78° C. at the end of treatment.

Similar results are found on films where, in the case of films treated by the process according to the invention, a temperature increase of denaturing starting temperature of 12° C. is observed.

(2) Collagenase digestion

To confirm the results obtained in differential calorimetry and to evaluate the performance of the materials relative to "aggressions" approaching those that are found in vivo, different materials (treated in the absence of salt, treated in the presence of sodium chloride, treated with GTA) were incubated for 7 days in the presence of bacterial collagenase (600 U/ml).

On the 7th day the amount of proteins in the supernatant was determined. The amount of proteins was proportional to the degree of attack by the collagenase.

The results are gathered in table II below:

TABLE II

| Treatment | Protein Level |
|---|---|
| Treated in the absence of NaCl | 105 micrograms/ml |
| Treated in the presence of 6% NaCl | 18 micrograms/ml |
| Treated 6% GTA | 6 micrograms/ml |

A very clearly improved behavior of the material is also noted when the treatment is performed in the presence of sodium chloride.

(3) Study of mechanical properties

The influence of the conditions of the chemical closing process on the physical properties of the collagen was studied on hog tendons. Unlike the pericardium, the tendon comprises collagen fibers all oriented in the same direction which facilitates interpretation of the results.

Figure 3:
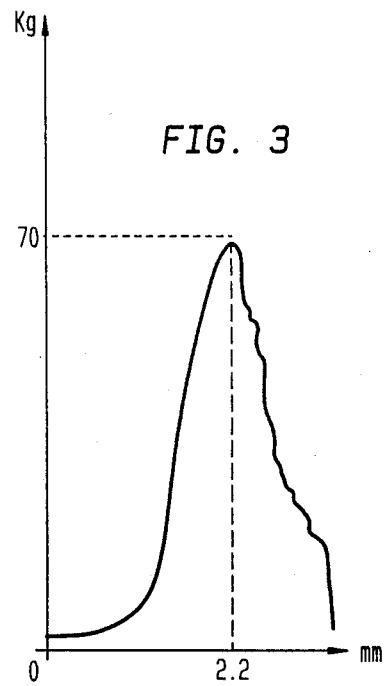
FIG. 3 and 4 are curves marking the physical properties (weight at break in kg on the X-axis, an elongation in mm on the Y-axis) respectively for a fresh tendon and a tendon treated according to the invention.
Figure 4:
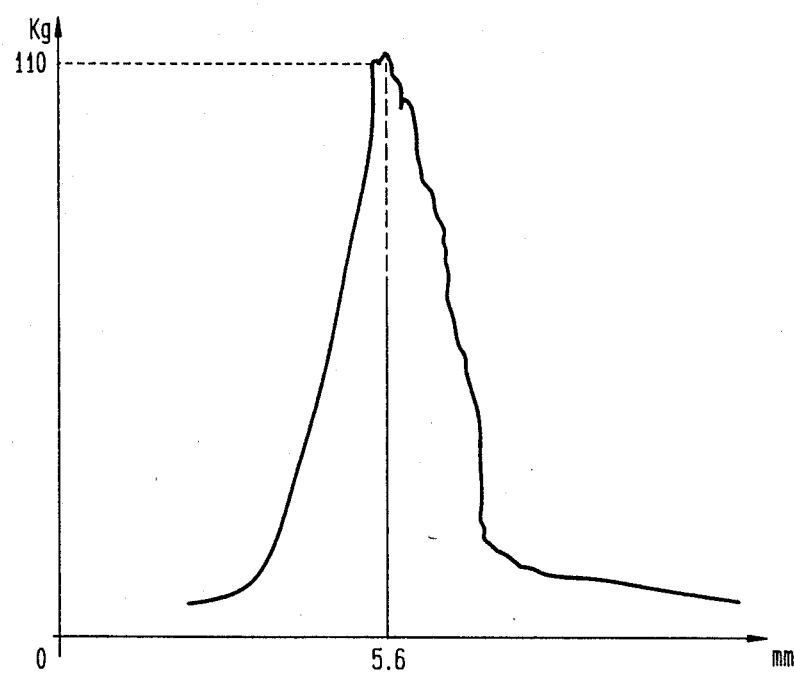

The results are gathered in table III and in FIGS. 3 and 4.

FIG. 3 is the curve of weight at break in kg as a function of elongation in mm for a fresh tendon and FIG. 4 is a similar curve for a tendon treated by the process according to the invention.

When the tendon is drawn, a curve is obtained from which it is possible to determine:
the mass at break: it is given by the maximum mass necessary for breaking the sample
deformation at break (extensibility at break): it is given by the ratio of elongation at break to the initial length of the sample,
the modulus of elasticity: this is the slope of the linear part of the curve; the greater the modulus of elasticity, the more rigid is the tissue.

Study of physical properties in uniaxial traction

| | Mass at break in kg in | Extensibility at break % | Modulus of elasticity in kg |
|---|---|---|---|
| fresh tendon | 46.42 ± 9 | 1.88 ± 0.6 | 1.38 |
| tendon activated by water | 87.83 ± 27.5 | 4.4 ± 0.92 | 7.8 ± 3.32 |
| tendon activated 6% NaCl | 87.33 ± 17.5 | 5.9 ± 1.2 | 8.75 ± 3.9 |
| tendon 0.6% GTA | 94.28 ± 16.57 | 7.14 ± 1.87 | 8. ± 1.9 |

The mass at break of the treated tissues are similar and significantly different from the mass at break of an untreated control tissue. Further, an increase is noted in the values of th extensibility at break for tissues treated according to the invention and tanned with GTA.

Finally, a significant increase is noted in the modulus of elasticity which is reflected by an increase in rigidity.

What is the explanation of the great differences stated above, particularly between materials subjected in a standard way to a crosslinking by introducing azide groups and materials treated according to the invention in the presence of sodium chloride?

When introduction of the azide groups is performed in the absence of sodium chloride, the hydrochloric acid causes, at the end of esterification, a swelling of the tissue; the latter then becomes thicker and translucent. The swelling corresponds to a limited dissolution of the tissue since there are numerous intermolecular and intramolecular bonds preventing a total dissolution of the tissue. At the end of esterification, the thermal stability of the tissue is that of an acid-soluble collagen (denaturing starting temperature is 36° C., the thickness of the pericardium goes from 0.38 mm to 0.82 mm).

At the other steps of the treatment, the phenomenon is identical but of less amplitude.

When introduction of the azide groups is performed under the conditions of the invention, i.e., in the presence of sodium chloride, at the end of esterification, a tissue is obtained, chloride, at the end of esterification, a tissue is obtained, which, from a macroscopic viewpoint, has not been modified.

In DSC, the thermal stability of the tissue thus treated is close to that of a fresh untreated tissue (the denaturing starting temperature is 53.9° C. for the tissue treated according to the invention and 58° C. for the fresh tissue).

Denaturation of the tissue is not observed during the other treatment steps.

In theory, it is possible to explain how the limiting action of the sodium chloride on the swelling takes place.

The collagen has polar side groups coming from basic and acidic amino acids.

Thus, depending on the pH of the medium, these groups will be ionized or not.

In acid medium: COOH and $NH_3^+$
In basic medium: $COO^-$ and $NH_2$

These ionizations explain the swelling phenomena, i.e., the absorption of water by the fiber.

Figure 5:
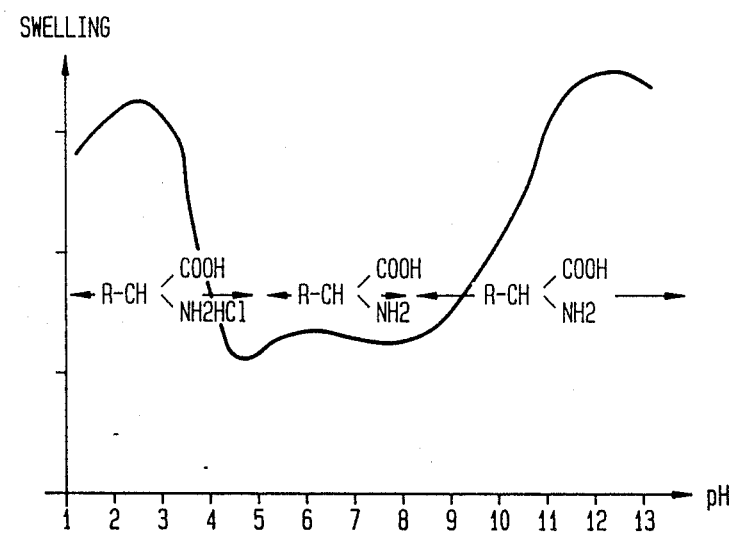
FIG. 5 is a curve marking the evolution of the swelling of a skin as a function of the pH.

They are well known in tanning and are used to facilitate depilation of hides. It is possible to establish swelling curves of the hide as a function of the pH (FIG. 5).

The esterification performed in the presence of hydrochloric acid causes fixing of the $H^+$ ions by the tissue. Thus, there will be an $H^+$ and $Cl^-$ migration from the aqueous phase to the collagen phase. To maintain electroneutrality, the chloride and hydrogen ions circulate in the form of molecules rather than as free ions. The hydrogen ions are fixed by the protein and the concentration of chloride ions of the fiber is greater than the concentration of chloride ions in the aqueous phase. In keeping with the law of mass action, the product of the concentration of chloride ions by the concentration of hydrogen ions should be equal in the fiber and in the aqueous phase. An osmotic pressure will then develop in the fiber which will increase the volume by absorbing water, hence a swelling of the pericardium.

The same reasoning can be used in the basic medium, when the tissue is in the presence of hydrazine (pH about 10).

In the presence of salt, there is a repression of the swelling of the tissue. Actually, in this case the difference in concentration in chloride ions is attenuated by the addition of sodium chloride. The osmotic pressure is slight and the swelling is reduced.

After esterification in the presence of salt, there are noted a constancy of the thickness of the tissue, an increase in the thermal stability; a 6% sodium chloride concentration has been found to be especially effective in obtaining a considerable good quality tanning.

To summarize, it seems that crosslinking of collagen by introduction of azide groups in the presence of sodium chloride makes it possible to obtain a crosslinked material of better quality than the same treatment in the absence of salt.

The crosslinked material in the presence of sodium chloride exhibits a certain number of properties (thermal stability, collagenase digestion) which are close to those of a material treated with glutaraldehyde.

Relative to a material treated with qlutaraldehyde, the material treated by the process according to the invention exhibits a clearly improved biocompatability.

Actually, the process according to the invention offers the great advantage of not introducing any foreign chemical agent into the collagen, while treatment with glutaraldehyde causes the fixing of substances that are cytotoxic and which, for this reason, cause the tissue to lose the essential of its biological properties.

Further, the tissue treated by the process according to the invention and implanted in a living organism will not release any toxic material able to have short-term or long-term disagreeable effects.

Of course, and as comes out from the above, the process that has just been described, applied to the pericardium can be applied to any other collagen tissue. It is suitable, of course, for achieving any reconstituted collagen-based biomaterial such as films, sponges, tubes, etc.

We claim:

1. Process of crosslinking collagen by introducing azide groups which essentially comprises the following steps:
   esterification of the free acid groups of collagen,
   transformation of the esterified groups into hydrazides groups,
   transformation of the hydrazide groups into azide groups by the action of nitrous acid, and is characterized in that each step is separated by a rinsing in an aqueous salt solution.

2. Process according to claim 1, wherein the step of transformation of esterified groups into azide groups and the step of transformation of hydrazide groups into azide groups by the action of nitrous acid, are performed in the presence of salt.

3. Process according to claims 1 or 2, wherein the salt is selected from alkaline metal salts.

4. Process according to claim 3, wherein the concentration of the aqueous salt solution is between 3 and 15%.

5. Process according to claim 4, wherein the crosslinking reaction by introduction of azide groups is performed on uncrosslinked collagens.

6. Application of the process of claim 1 for obtaining bioprotheses.

7. Application of the process according to claim 1 for obtaining biomaterials.

8. Application of the process of claim 2 for obtaining bioprotheses.

9. Application of the process of claim 3 for obtaining bioprotheses.

10. Application of the process of claim 4 for obtaining bioprotheses.

11. Application of the process of claim 5 for obtaining bioprotheses.

12. Application of the process according to claim 2 for obtaining biomaterials.

13. Application of the process according to claim 3 for obtaining biomaterials.

14. Application of the process according to claim 4 for obtaining biomaterials.

15. Application of the process according to claim 5 for obtaining biomaterials.

* * * * *

UNITED STATES PATENT AND TRADEMARK OFFICE
CERTIFICATE OF CORRECTION

PATENT NO. : 4,958,008
DATED : September 18, 1990
INVENTOR(S) : PETITE et al.

It is certified that error appears in the above-identified patent and that said Letters Patent is hereby corrected as shown below:

Title page:

[73] Assignees: BIOETICA, Lyon, France
INSTITUT NATIONAL DE LA SANTE ET DE LA
RECHERCHE MEDICALE (INSERM), Paris, France Signed and Sealed this Seventh Day of July, 1992

Attest:

DOUGLAS B. COMER

*Attesting Officer*  Acting Commissioner of Patents and Trademarks